United States Patent [19]

Higa

[11] Patent Number: 5,089,643

[45] Date of Patent: Feb. 18, 1992

[54] METHOD OF PREPARING MONOMERIC ORGANOMETALLIC COMPOUNDS

[75] Inventor: Kelvin T. Higa, Ridgecrest, Calif.

[73] Assignee: The United States of America as represented by the Secretary of the Navy, Washington, D.C.

[21] Appl. No.: 694,267

[22] Filed: Apr. 29, 1991

Related U.S. Application Data

[62] Division of Ser. No. 534,997, Jun. 8, 1990.

[51] Int. Cl.$^5$ .............................. C07F 5/00; C07F 5/06
[52] U.S. Cl. ........................................... 556/1; 556/20; 556/70; 556/29; 556/170; 556/174; 556/176
[58] Field of Search ................. 556/20, 29, 1, 70, 170, 556/174, 176

[56] References Cited

U.S. PATENT DOCUMENTS 5,003,092  3/1991  Beachley, Jr. ..................... 556/1
5,015,747  5/1991  Hostalek et al. ................... 556/1
5,030,741  7/1991  Erdmann et al. ................... 556/1

FOREIGN PATENT DOCUMENTS 3631469  3/1988  Fed. Rep. of Germany ...... 556/174

Primary Examiner—Jose G. Dees
Assistant Examiner—Porfirio Nazario—Gonzalez
Attorney, Agent, or Firm—Stuart H. Nissim; Melvin J. Sliwka; Sol Sheinbein

[57] ABSTRACT

Preparation of the novel monomeric compounds of the formula $(t-Bu)_2ME(t-Bu)_2$, where M is Ga, Al, or In and E is As, P, Sb, or N, by reaction of $(t-Bu)_2MCl$ and $LiE(t-Bu)_2$. The resulting product $(t-Bu)_2ME(t-Bu)_2$ can be pyrolyzed to form crystalline films of the metallic material, ME.

21 Claims, No Drawings

METHOD OF PREPARING MONOMERIC ORGANOMETALLIC COMPOUNDS

This is a divisional of co-pending application Ser. No. 07/534,997 filed on June 8, 1990.

BACKGROUND OF THE INVENTION

This invention relates to the production of organometallic compounds, and is particularly directed to the preparation of certain volatile monomeric III-V compounds which can be pyrolyzed to form films of the corresponding metallic compound.

Single source organometallic precursors have been utilized to prepare epitaxial films of GaP, GaAs and InP. Although arsinogallanes have been known for over 25 years, monomeric arsinogallanes are rare. Arsinogallanes are usually found as dimers, trimers or adducts due to the proclivity of Ga(III) toward tetracoordination. Attempts to prepare monomeric arsinogallanes have focused on the use of bulky substituents. The first monomeric arsinogallane, [(Mesityl)$_2$As]$_3$Ga, was reported in 1986 by Wells et al, Inorg. Chem., 1986, 25,2483. Cowley et al., reported a dimer of a t-Butyl derivative arsinogallane compound, [(t-Bu)$_2$AsGa(CH$_3$)$_2$]$_2$, J. Chem. Soc., Chem. Commun., 1986, 1543; this compound is a solid having low vapor pressure. Only recently, Theopold et al., SCIENCE, 1988, 241, 334, reported the first mono(arsino)gallane monomer, (C$_5$(CH$_3$)$_5$)$_2$GaAs(Si(CH$_3$)$_3$)$_2$, and its conversion to amorphous GaAs powder via reaction with alcohol; this compound is also a solid having negligible vapor pressure.

One object of the invention is the provision of novel monomeric organometallic compounds.

Another object is to provide a novel class of organometallic compounds which are volatile and can be readily converted to their respective metallic compounds.

A still further object is the provision of procedure for preparing the above volatile organometallic compounds.

Yet another object is to provide procedure for readily converting the above organometallic compounds to their respective metallic compounds, e.g., as films.

SUMMARY OF THE INVENTION

The above objects are achieved according to the invention by provision of the novel monomeric organometallic compounds having the formula (t-Bu)$_2$ME(t-Bu)$_2$, where M is Ga, Al, or In and E is As, P, Sb, or N, by reacting (t-Bu)$_2$MCl and LiE(t-Bu)$_2$, in a molar ratio of about 1:1, preferably in a non-polar solvent such as benzene The resulting monomeric mono(III-V) compounds, (t-Bu)$_2$ME(t-Bu)$_2$, are relatively volatile and can be pyrolyzed to form relatively pure crystalline III-V (metallic) deposits and films, at relatively low pyrolysis temperatures.

DETAILED DESCRIPTION OF THE INVENTION AND PREFERRED EMBODIMENTS

According to the invention, monomeric organometallic compounds of the type (t-Bu)$_2$ME(t-Bu)$_2$ can be prepared from the reaction of (t-Bu)$_2$MCl and LiE(t-Bu)$_2$ according to the following reaction scheme:

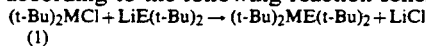

(1)

where
M is Ga, Al, or In; and,
E is As, P, Sb, or N.

The molar ratio of the reactants (t-Bu)$_2$MCl and LiE(t-Bu)$_2$ is 1:1, but a small excess of the lithium-containing reactant, LiE(t-Bu)$_2$, is generally employed.

The above reaction is carried out in a non-polar solvent such as pentane, hexane, benzene or toluene. The reaction is generally carried out at ambient temperature and under an inert atmosphere such as argon, but the temperature of the reaction can be varied.

Following completion of the reaction, the solvent can be removed, e.g. under vacuum, and the product can be purified, as by sublimation, followed by recrystallization.

The products of the above reaction are volatile monomeric mono(III-V) compounds such as mono(arsinogallane), (t-Bu)$_2$GaAs(t-Bu)$_2$ and mono(phosphinogallane), (t-Bu)$_2$GaP(t-Bu)$_2$. Such monomeric organometallic products can be pyrolyzed in a vacuum or an inert atmosphere such as argon or helium, at a temperature significantly lower than possible with prior art compounds. The pyrolysis reaction scheme is as follows:

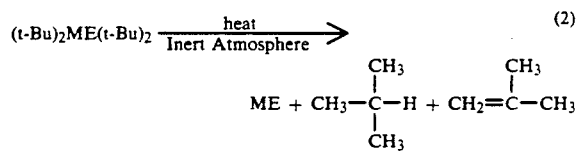

(2)

where
M is as described above, and
E is as described above.

Alternatively, the above pyrolysis reaction can be carried out under a vacuum.

The above pyrolysis reaction can be utilized for depositing III-V metallic films employed as semi-conductors in electronics.

The above monomeric organometallic products of the invention can also be subjected to metal-organic chemical vapor deposition for depositing films.

The advantages of the products, (t-Bu)$_2$ME(t-Bu)$_2$, of the invention are: (1) the lower vapor pressure and reduced air-sensitivity reduces the toxicity (e.g.,AsH$_3$) and safety hazards (e.g., flammability of (CH$_3$)$_3$Ga) of the materials presently used in film deposition by the metal-organic chemical vapor deposition (MOCVD) process; (2) the utilization of t-butyl groups, which can undergo beta-elimination reactions during pyrolysis tends to result in lower carbon incorporation into the deposited metallic film; (3) hiqhly crystalline films can be prepared by pyrolysis at less than 550° C.; (4) electronic grade purity of the metallic deposits can be achieved through multiple sublimations; and (5) the correct stoichiometry of Group III to Group V materials is always maintained.

In addition to the use of the materials produced according to the invention process as semiconductor films, such materials also have utility for infrared transparent domes of missiles, since these materials have good physical properties including good strength, thermal stability and thermal shock resistance, and have good optical or infrared transparency.

The following are examples of practice of the invention, which are understood as being illustrative and are not intended as limitative of the invention.

EXAMPLE 1

Benzene (20ml) was added to (t-Bu)$_2$GaCl (0.66 g, 3.0 mmol) and LiAs(t-butyl)$_2$ (0.60 g, 3.1 mmol) at room temperature. After stirring for 2.5 days under argon, the yellow-orange solution was filtered using a fine frit and the solvent removed under vacuum to give crude (t-Bu)$_2$GaAs(t-Bu)$_2$ (1.1 g 2.9 mmol, 97% yield) as a yellow orange liquid. The product, which began to sublime at 18° C. at $10^{-3}$ torr, was purified by sublimation at 65° C. at $10^{-3}$ torr. Recrystallization in pentane at −78° C gave yellow crystals suitable for x-ray analysis, mp 41–44° C. See NMR Table 1.

Two isopiestic molecular weight determinations in pentane gave molecular weights of 419 and 395, which are consistent with a monomeric structure (molecular weight of 373) in solution. The low melting point of 41–44° C., the mass spectrum and molecular weight determination of (t-Bu)$_2$GaAs(t-Bu)$_2$ were all indicative of a monomeric structure in the solid, gas and liquid states. A single-crystal x-ray structure was performed to confirm the nature of the product. The stabilization of the monomeric unit is due to the fact that the Ga and As atoms are effectively shielded from intermolecular association by the bulky t-butyl substituents on both gallium and arsenic.

EXAMPLE 2

The process of Example 1 was substantially followed except LiP(t-Bu)$_2$ was substituted for LiAs(t-Bu)$_2$ in the same molar proportions with respect to (t-Bu)$_2$GaCl.

The monomeric phosphinogallane, (t-Bu)$_2$GaP(t-Bu)$_2$, was produced. Mp. 46–48 C. $^{31}$P NMR 23.9. See NMR Table 1.

EXAMPLE 3

The process of Example 1 was substantially followed except (t-Bu)$_2$AlCl was substituted for (t-Bu)$_2$GaCl in the same molar proportions with respect to LiAs(t-Bu)$_2$.

The monomeric arsinoalane, (t-Bu)$_2$AlAs(t-Bu)$_2$, was produced. See NMR Table 1.

EXAMPLE 4

The process of Example 1 was substantially followed except LiP(t-Bu)$_2$ was substituted for LiAs(t-Bu)$_2$ in the same molar proportions with respect to (t-Bu)$_2$AlCl which was substituted for (t-Bu)$_2$GaCl. The monomeric phosphinoalane, (t-Bu)$_2$AlP(t-Bu)$_2$, was produced. See NMR Table 1.

EXAMPLE 5

The process of Example 1 was substantially followed except (t-Bu)$_2$InCl was substituted for (t-Bu)$_2$GaCl in the same molar proportions with respect to LiAs(t-Bu)$_2$.

The monomeric arsinoindane, (t-Bu)$_2$InAs(t-Bu)$_2$, was produced. See NMR Table 1.

EXAMPLE 6

The process of Example 1 was substantially followed except LiP(t-Bu)$_2$ was substituted for LiAs(t-Bu)$_2$ in the same molar proportions with respect to (t-Bu)$_2$InCl which was substituted for (t-Bu)$_2$GaCl.

The monomeric phosphinoindane, (t-Bu)$_2$InP(t-Bu)$_2$, was produced.

EXAMPLE 7

The process of Example 1 is substantially followed except LiSb(t-Bu)$_2$ or LiN(t-Bu)$_2$ is substituted for LiAs(t-Bu)$_2$ in the same molar proportions with respect to (t-Bu)$_2$GaCl, or to (t-Bu)$_2$AlCl or (t-Bu)$_2$InCl which is substituted for (t-Bu)$_2$GaCl.

The respective monomeric compound: (t-Bu)$_2$GaSb(t-Bu)$_2$, (t-Bu)$_2$GaN(t-Bu)$_2$, (t-Bu)$_2$AlSb(t-Bu)$_2$, (t-Bu)$_2$AlN(t-Bu)$_2$, (t-Bu)$_2$InSb(t-Bu)$_2$, or (t-Bu)$_2$InN(t-Bu)$_2$ is produced.

EXAMPLE 8

(t-Bu)$_2$GaAs(t-Bu)$_2$ was heated to 150° C. for 10 min. without decomposition, but decomposed to red oligomers and/or polymers at 188–190° C. Pyrolysis of monomeric mono(arsino) gallane, (t-Bu)$_2$GaAs(t-Bu)$_2$, under a Helium atmosphere with a cool yellow flame (400° C.) resulted in crystalline GaAs and approximately a 1:1 mole ratio of 2-methylpropane and 2-methylpropene. The decomposition can be rationalized by either a beta-elimination followed by alkane elimination (reaction scheme 2), or a free radical mechanism or both.

EXAMPLE 9

(t-Bu)$_2$GaP(t-Bu)$_2$ was pyrolyzed under substantially the same reaction conditions as noted in Example 8, resulting in the formation of crystalline GaP.

EXAMPLE 10

(t-Bu)$_2$AlP(t-Bu)$_2$, (t-Bu)$_2$AlAs(t-Bu)$_2$, (t-Bu)$_2$InP(t-Bu)$_2$, (t-Bu)$_2$InAs(t-Bu)$_2$, (t-Bu)$_2$InSb(t-Bu)$_2$, (t-Bu)$_2$InN(t-Bu)$_2$, (t-Bu)$_2$GaSb(t-Bu)$_2$, (t-Bu)$_2$GaN(t-Bu)$_2$, (t-Bu)$_2$AlSb(t-Bu)$_2$, or (t-Bu)$_2$AlN(t-Bu)$_2$ is pyrolyzed under a vacuum or inert atmosphere, e.g., helium, resulting in the formation of crystalline AlP, AlAs, InP, InAs, InSb, InN, GaSb, GaN, AlSb and AlN respectively.

TABLE 1

| | | NMR of (t-Butyl)$_2$M—E(t-Butyl)$_2$ | |
|---|---|---|---|
| M | E | (t-Bu)$_2$M | E(t-Bu)$_2$ |
| Al | P | 1.27d($^4J_{PH}$=0.5Hz) | 1.53($^3J_{PH}$=11Hz) |
| Ga | P | 1.27d($^4J_{PH}$=2.0Hz) | 1.30($^3J_{PH}$=9Hz) |
| Al | As | 1.29s | 1.57s |
| Ga | As | 1.26s | 1.40s |
| In | As | 1.24s | 1.40s |

From the foregoing, it is seen that the invention provides for the preparation of a novel class of volatile monomeric organometallic materials which can by pyrolyzed readily at relatively low temperatures, to form essentially pure electronic grade metallic deposits or films.

Since various changes and modifications can be made in the invention without departing from the spirit of the invention, the invention is not to be taken as limited except by the scope of the appended claims.

What I now claim as my invention is:

1. A process for preparing monomeric organometallic compounds which comprises:
   reacting (t-Bu)$_2$MCl and LiE(t-Bu)$_2$, and recovering a compound having the formula (t-Bu)$_2$ME(t-Bu)$_2$; where,
   M is selected from the group consisting of Ga, Al, and In, and E is selected from the group consisting of As, P, Sb, and N.

2. The process of claim 1 employing LiAs(t-Bu)$_2$ for reaction with (t-Bu)$_2$GaCl and recovering (t-Bu)$_2$GaAs(t-Bu)$_2$.

3. The process of claim 1, employing LiP(t-Bu)$_2$ for reaction with (t-Bu)$_2$GaCl, and recovering (t-Bu)$_2$GaP(t-Bu)$_2$.

4. The process of claim 1, employing LiAs(t-Bu)$_2$ for reaction with (t-Bu)$_2$AlCl, and recovering (t-Bu)$_2$AlAs(t-Bu)$_2$.

5. The process of claim 1, employing LiN(t-Bu)$_2$ for reaction with (t-Bu)$_2$AlCl, and recovering (t-Bu)$_2$AlN(t-Bu)$_2$.

6. The process of claim 1, employing LiAs(t-Bu)$_2$ for reaction with (t-Bu)$_2$InCl, and recovering (t-Bu)$_2$InAs(t-Bu)$_2$.

7. The process of claim 1, employing LiP(t-Bu)$_2$ for reaction with (t-Bu)$_2$InCl, and recovering (t-Bu)$_2$InP(t-Bu)$_2$.

8. The process of claim 1, employing LiSb(t-Bu)$_2$ for reaction with (t-Bu)$_2$GaCl and recovering (t-Bu)$_2$GaSb(t-Bu)$_2$.

9. The process of claim 1, employing LiN(t-Bu)$_2$ for reaction with (t-Bu)$_2$GaCl, and recovering (t-Bu)$_2$GaN(t-Bu)$_2$.

10. The process of claim 1, employing LiSb(t-Bu)$_2$ for reaction with (t-Bu)$_2$AlCl, and recovering (t-Bu)$_2$AlSb(t-Bu)$_2$.

11. The process of claim 1, employing LiN(t-Bu)$_2$ for reaction with (t-Bu)$_2$AlCl, and recovering (t-Bu)$_2$AlN(t-Bu)$_2$.

12. The process of claim 1, employing LiSb(t-Bu)$_2$ for reaction with (t-Bu)$_2$InCl, and recovering (t-Bu)$_2$InSb(t-Bu)$_2$.

13. The process of claim 1, employing LiN(t-Bu)$_2$ for reaction with (t-Bu)$_2$InCl, and recovering (t-Bu)$_2$InN(t-Bu)$_2$.

14. The process of claim 1, the molar ratio of (t-Bu)$_2$MCl, and LiE(t-Bu)$_2$ being about 1:1.

15. The process of claim 14, said reaction taking place in a non-polar solvent at about ambient temperature and in an inert atmosphere.

16. A process for preparing (t-Bu)$_2$GaAs(t-Bu)$_2$, which comprises reacting (t-Bu)$_2$GaCl and LiAs(t-Bu)$_2$ in a molar ratio of about 1:1 in a non-polar solvent at about ambient temperature and in an inert atmosphere, removing the solvent and recovering (t-Bu)$_2$GaAs(t-Bu)$_2$.

17. A process for preparing (t-Bu)$_2$GaP(t-Bu)$_2$, which comprises reacting (t-Bu)$_2$GaCl and LiP(t-Bu)$_2$ in a molar ratio of about 1:1 in a non-polar solvent at about ambient temperature and in an inert atmosphere, removing the solvent and recovering (t-Bu)$_2$GaP(t-Bu)$_2$.

18. A process for preparing (t-Bu)$_2$AlAs(t-Bu)$_2$, which comprises reacting (t-Bu)$_2$AlCl and LiAs(t-Bu)$_2$ in a molar ratio of about 1:1 in a non-polar solvent at about ambient temperature and in an inert atmosphere, removing the solvent and recovering (t-Bu)$_2$AlAs(t-Bu)$_2$.

19. A process for preparing (t-Bu)$_2$AlP(t-Bu)$_2$, which comprises reacting (t-Bu)$_2$AlCl and LiP(t-Bu)$_2$ in a molar ratio of about 1:1 in a non-polar solvent at about ambient temperature and in an inert atmosphere, removing the solvent and recovering (t-Bu)$_2$AlP(t-Bu)$_2$.

20. A process for preparing (t-Bu)$_2$InAs(t-Bu)$_2$, which comprises reacting (t-Bu)$_2$InCl and LiAs(t-Bu)$_2$ in a molar ratio of about 1:1 in a non-polar solvent at about ambient temperature and in an inert atmosphere, removing the solvent and recovering (t-Bu)$_2$InAs(t-Bu)$_2$.

21. A process for preparing (t-Bu)$_2$InP(t-Bu)$_2$, which comprises reacting (t-Bu)$_2$InCl and LiP(t-Bu)$_2$ in a molar ratio of about 1:1 in a non-polar solvent at about ambient temperature and in an inert atmosphere, removing the solvent and recovering (t-Bu)$_2$InP(t-Bu)$_2$.

* * * * *